United States Patent
Hindi et al.

(10) Patent No.: US 7,479,138 B2
(45) Date of Patent: Jan. 20, 2009

(54) LASER PULSE POSITION MONITOR FOR SCANNED LASER EYE SURGERY SYSTEMS

(75) Inventors: David Hindi, San Jose, CA (US); Keith Holliday, San Jose, CA (US); Mark Arnoldussen, San Carlos, CA (US)

(73) Assignee: AMO Manufacturing USA, LLC, Santa Clara, CA (US)

( * ) Notice: Subject to any disclaimer, the term of this patent is extended or adjusted under 35 U.S.C. 154(b) by 399 days.

(21) Appl. No.: 11/174,279

(22) Filed: Jun. 30, 2005

(65) Prior Publication Data

US 2006/0084955 A1    Apr. 20, 2006

Related U.S. Application Data

(60) Provisional application No. 60/586,557, filed on Jul. 9, 2004.

(51) Int. Cl.
*A61F 9/008* (2006.01)
(52) U.S. Cl. .................. 606/11; 606/5; 606/10
(58) Field of Classification Search ........... 606/3–7, 606/10–13
See application file for complete search history.

(56) References Cited

U.S. PATENT DOCUMENTS

| | | | |
|---|---|---|---|
| 5,928,221 A | 7/1999 | Sasnett et al. | |
| 6,210,169 B1 | 4/2001 | Yavitz | |
| 6,210,401 B1 | 4/2001 | Lai | |
| 6,322,555 B1 | 11/2001 | LaHaye | |
| 6,325,792 B1 | 12/2001 | Swinger et al. | |
| 6,559,934 B1 | 5/2003 | Yee et al. | |
| 6,666,855 B2 | 12/2003 | Somani et al. | |
| 6,817,998 B2 | 11/2004 | LaHaye | |
| 2001/0056276 A1 | 12/2001 | LaHaye | |
| 2002/0077622 A1 | 6/2002 | Hofer | |
| 2003/0144650 A1 | 7/2003 | Smith | |
| 2003/0149426 A1 | 8/2003 | Yee et al. | |
| 2005/0215986 A1 | 9/2005 | Chernyak et al. | |

FOREIGN PATENT DOCUMENTS

| | | | |
|---|---|---|---|
| CA | 2065174 A | * | 10/1992 |
| WO | WO 02/076319 A1 | | 10/2002 |

OTHER PUBLICATIONS

Wikipedia entry: Photodiode, May 14, 2004 version, 2 pages.*
Product Specification sheet for DL-100-7-KER from Pacific Silicon Sensor, Inc.; Feb. 9, 2006; 2 pages.*

(Continued)

*Primary Examiner*—David Shay
(74) *Attorney, Agent, or Firm*—Townsend and Townsend and Crew LLP (57) ABSTRACT

Devices, systems, and methods for measuring and determining positions of light energy having wavelengths of less than (as well as equal to or greater than) 200 nm, and are particularly well suited for measuring pulsed light at ultraviolet and other wavelengths using position sensing diode (PSD) technology. An integrator may sum a total charge of a signal from the PSD. Correlations between a distribution of integrated charges among electrodes of the PSD may be non-linear, and may benefit from adjustment for different overall pulse light quantities and/or spot sizes.

27 Claims, 3 Drawing Sheets

OTHER PUBLICATIONS

Product Specifications for PSM series Position Sensing Modules F25 series and F12.5 series from On-Trac Photonics, Inc.; 4 pages.*

Position Sensing Detectors Theory of Operations. Datasheet [online]. On-Trak Photonics, Inc. [retrieved on Jan. 13, 2004] Retrieved from the Internet <URL: http://www.on-trak.com/theory.html>.

Position Sensing Detectors—PSD—Lasers, 1L Series. Datasheet [online]. On-Trak Photonics, Inc. [retrieved on Jan. 13, 2004] Retrieved from the Internet <URL: http://www.on-trak.com/1lseries.html>.

2L Series. Datasheet [online]. On-Trak Photonics, Inc. [retrieved on Jan. 13, 2004] Retrieved from the Internet <URL: http://www.on-trak.com/2lseries.html>.

* cited by examiner

FIG_4

Fig. 5

LASER PULSE POSITION MONITOR FOR SCANNED LASER EYE SURGERY SYSTEMS

CROSS-REFERENCES TO RELATED APPLICATIONS

This application is a nonprovisional U.S. patent application which claims the benefit under 35 USC 119(e) of U.S. Provisional Patent Application No. 60/586,557 filed Jul. 9, 2004, the full disclosure of which is incorporated herein by reference.

BACKGROUND OF THE INVENTION

The present invention generally provides devices, systems, and methods for determining a position of an electromagnetic energy beam. In many embodiments, the invention provides methods and devices for determining positions of pulsed laser beams having wavelengths of less than 200 nm such as the excimer laser beams used in refractive surgery.

Refractive surgery has changed dramatically over the last several years with the introduction and acceptance of refractive laser eye surgery techniques. Laser eye surgery often employs a laser to effect ablative photodecomposition of corneal tissues, thereby resculpting the ocular optics and correcting vision defects. Ultraviolet laser-based systems often direct a pattern of energy pulses on to the cornea in a controlled manner so as to effect a desired change in the corneal surface shape.

While early refractive laser surgery systems employed variable or ablatable masks to provide progressive shaping of the laser beam, most current refractive laser systems controllably deflect the laser beam so as to scan a laser spot over the exposed corneal surface. The laser will often be used to selectively remove stromal tissues from within the cornea, typically after the overlying epithelial tissue has been removed or temporarily displaced in procedures referred to as photorefractive keratectomy (PRK) or laser assisted subepithelial keratomileusis (LASEK) and laser in situ keratomileusis (LASIK), respectively. The size of the laser spot on the cornea may or may not be changed during a refractive procedure, and the laser energy is most often delivered as a series of discrete laser pulses, with each pulse removing a portion of the overall ablation shape.

The use of scanned or "flying spot" laser delivery systems can significantly increase the flexibility of a refractive treatment, particularly for treatment of hyperopic, astigmatic, and irregular refractive errors. However, the use of such movable beam systems can complicate certain aspects of the treatment protocols. For example, to achieve a desired resculpting of the corneal tissue, the treatment beam is scanned or otherwise moved across the eye to a large number of different positions. Movement of the beam may be achieved using motorized scanning mechanisms, including offset lenses, movable mirrors, galvanometric actuators, and the like. To achieve the desired resculpting the position of the scanned laser beam should be controlled and/or monitored accurately. If the beam inadvertently resides at one position for too long, due to a jam or malfunction of the scanning mechanism or control system (for example) the desired tissue ablation pattern may not be achieved. In fact, a jam of the scanning system may jeopardize the success of the surgery and could cause damage to the patient's eye. Malfunctions of a scanning mechanism may not be readily detectable by an observer.

To ensure the safety and accuracy of laser refractive procedures, a variety of motion detector systems for corneal laser delivery systems have been developed. Techniques have also been developed for calibrating laser eye surgery systems, determining the characteristics of a laser beam spot, and the like. Exemplary structures are described in U.S. patent application Ser. No. 10/383,445, in U.S. Pat. No. 6,666,855, and in U.S. patent application Ser. No. 10/760,112, as well as U.S. patent application Ser. No. 10/808,728, the full disclosures of which are incorporated herein by reference. While these and other systems have proven effective and safe for monitoring the position of a laser beam for refractive surgeries, as with many successes, still further improvements would be desirable. More specifically, many techniques for determining a position of the laser beam rely on charge couple devices (CCDs) with associated pixel image processing so as to determine a location of a scanned beam. While generally effective, these systems can be fairly complex and expensive, and may have a resolution that is limited by pixel density. The output from the systems may reflect the digital nature of these pixel-based sensors, and the processing time may increase the amount of data processing capability needed for the system and/or may limit the cycle time for positioned confirmation.

A variety of other fields also make use of systems for monitoring or detecting the position of a laser beam. One structure that has been gaining popularity in recent years is the position sensing diode (PSD). PSDs are silicon photodiodes that provide an analog output directly proportional to the position of a light spot on a surface of the detector. PSDs allow simultaneous monitoring of position and light intensity, with the photo generated current from a PSD being proportional to the position of an incident spot of continuous light when the light is within a wavelength range of the PSD. As relatively simple analog devices, PSDs have advantages over CCDs and other pixel-based devices using image processing to determine a location of a light beam.

Unfortunately, existing PSDs are often limited to measurements of continuous incident light beams having a wavelength of over 200 nm, with responsivity of these structures often benefiting from incident wavelengths of at least 400 nm or more. Hence, despite their potential advantages, PSDs have not been widely used for measuring, monitoring, and confirming positions of pulsed laser beams such as those used in laser refractive eye surgery.

In light of the above, it would be advantageous to provide improved devices, systems, and methods for determining positions of laser and other light energy beams. It would be particularly advantageous if these improvements provided the benefits available from position sensing silicon photodiodes, but expanded those benefits to laser eye surgery systems and other pulsed light-beam scanning and/or positioning systems.

BRIEF SUMMARY OF THE INVENTION

The present invention generally provides improved devices, systems, and methods for measuring and determining positions of light energy. The techniques of the present invention are suitable for measuring light having wavelengths of less than (as well as equal to or greater than) 200 nm, and are particularly well suited for measuring pulsed light at ultraviolet and other wavelengths. The invention takes advantage of position sensing diode (PSD) technology, but rather than relying on a steady state current or voltage drop, the invention will often use an integrator to sum a total charge that flows from the PSD. Correlations between a distribution of integrated charges among electrodes of the PSD may be non-linear (often contrasting with the standard PSD position/signal linear relationship), and may benefit from adjustment for different overall incident light quantities and/or spot sizes.

Advantageously, an integrated signal from a PSD for a single pulse of light energy allows position and/or light energy of the pulse to be reliably and accurately determined, possibly even when a manufacturer of the PSD believes that the light energy to be measured may be beyond the capabilities of the PSD.

In a first aspect, the invention provides a method for determining a position of a pulsed beam. The method comprises positioning a position sensing diode in a path of the beam. The position sensing diode generates a pulse of current in response to a pulse of the beam. The initial pulse of current is integrated to generate an integrated charge signal. A position of the pulse on the position sensing diode is determined in response to the integrated charge signal.

The pulsed beam may comprise a laser beam having a wavelength of less than 220 nm. In the exemplary embodiment, the pulsed laser beam may have a wavelength in a range from about 190 nm to about 196 nm. The pulsed beam may be capable of photo ablating corneal tissue. The beam may be separated, with a first portion of the beam being directed along the optical path toward the position sensing diode. A second portion of the beam may be directed along another optical path toward an eye of a patient so that the beam changes a refraction of the eye while a position of the beam on the eye is determined using the position sensing diode. The pulsed beam may be generated using an excimer laser.

The position sensing diode may have a sensing surface and a plurality of electrodes. The initial signal may have a total charge associated with the pulse. The integration may sum at least two portions of the total charge. The summed portion or portions may be associated with two or more electrodes of the position sensing diode. The integration of the initial signal may comprise summing a plurality of charge portions for an associated plurality of electrodes, and the pulse position may be determined using a distribution of the charge portions between those electrodes. A total amount of light at the sensing surface of the position sensing diode may be determined from the charge portions at the electrodes.

A position of the pulse along an X axis of the sensing surface may be determined using a linear or non-linear correlation between the X position and the distribution of the total charge between a first X electrode and a second X electrode. Similarly, the sensing surface may comprise an X-Y sensing surface, with the position of the pulse along a Y axis of the sensing surface being determined using a linear or non-linear correlation between the Y position and a distribution of the total charge between a first Y electrode and a second Y electrode.

The position sensing diode may comprise a silicon photodiode having a plurality of electrodes. The initial signal may be integrated using a plurality of analog integrator circuits, with each integrator circuit being coupled to an associated electrode. In many embodiments, the integration may be performed by an integrator, and a plurality of positions of a plurality of pulses of the beam will be determined. The integrator will often be reset between at least some of the pulses. The pulsed beam may have a beam pulse frequency of up to 1 KHz.

In another aspect, the invention provides an apparatus comprising a light source for directing a pulsed light beam along an optical path. A position sensing diode is disposed in the optical path so as to generate a signal in response to a pulse of the beam. An integrator is coupled to the position sensing diode so as to integrate the signal for the pulse to generate a charge signal. A position module is coupled to the integrator, and is configured to determine a position of the pulse on the position sensing diode in response to the charge signal.

A wavelength of the pulsed beam will often be less than 220 nm, the light source optionally comprising an excimer laser such that the pulsed laser beam has a wavelength in a range from about 190 nm to about 196 nm.

A beam deflector may be disposed along the optical path from the light source and a beam splitter may be disposed along the optical path from the beam deflector. The beam splitter may separate the beam and direct a first portion of the beam along the optical path toward the position sensing diode. A second portion of the beam may be directed along another optical path, so that when the beam deflector variably redirects the beam the position module indicates a position of the second portion of the beam.

The position sensing diode may have a sensing surface and a plurality of electrodes. The integrator may be coupled to at least two of the electrodes. The signal may include a total charge associated with the pulse. The integrator may generate the charge signal by summing at least two portions of the total charge directed to an associated electrode. The pulse position may be determined using the at least two charge portions.

The integrator may sum the plurality of charge portions at an associated plurality of electrodes. The position module may be configured to determine a total charge at the electrodes, with the total charge correlating to an amount of light at the sensing surface. The position module may be configured to apply a correlation between the pulse position and a distribution of the charge portions between the plurality of electrodes. The correlation may be non-linear.

The positioned module may be configured to determine a position of the pulse along an X axis of the sensing surface from a distribution of the total charge between a first X electrode and a second X electrode. The sensing surface will often comprise an X-Y sensing surface, and a position module may be configured to determine a position of the pulse along a Y axis of the sensing surface from a distribution of the total charge between the first Y electrode and a second Y electrode.

The position sensing diode may comprise a silicon photodiode having a plurality of electrodes. The integrator may comprise a plurality of analog integrator circuits, each integrator circuit coupled to an associated electrode. The position module may be configured to determine a plurality of positions of a plurality of pulses of the beam, and the integrator may be reset between at least some of the pulses.

In another aspect, the invention provides an apparatus for altering a refraction of an eye. The apparatus comprises a laser for directing a pulsed laser upon an optical path. The laser beam has a wavelength of less than 220 nm. A beam deflector is disposed along the optical path from the laser. The beam deflector variably redirects the beam, and a beam splitter is disposed along the optical path from the beam deflector. The beam splitter separates the laser beam and directs a first portion of the laser beam along the optical path and a second path of the laser beam along another optical path toward the eye. A position sensing diode is disposed in the optical path so as to generate a signal in response to a pulse of the laser beam. An integrator is coupled to the position sensing diode so as to integrate the signal for the pulse to generate a charge signal. A position module is coupled to the integrator. The position module is configured to indicate a position of the beam on the eye in response to the charge signal.

The apparatus may also include a variable aperture for varying a size of a laser spot on the eye during the refractive treatment. The position module may determine the position in response to the laser spot size. The wavelength of the laser beam will often be less than 220 nm.

DETAILED DESCRIPTION OF THE INVENTION

The present invention generally provides improved devices, systems, and methods for measuring light beams. The systems of the present invention will generally include position sensing diode (PSD) silicon photodiodes that provide an analog output. As the devices, systems, and methods of the invention allow the accurate use of position sensing diodes for both wavelengths which were known to be compatible with PSDs and for wavelengths which were previously thought to be incompatible with these analog devices, the techniques of the invention may expand the use of these accurate, simple, and low-cost structures. By use of the inventions described herein, position sensing diodes may be used to accurately measure position and/or light energy of pulsed beams having wavelengths of less than 300 nm, the beams optionally having wavelengths of 220 nm or less, the beams often having wavelengths of less than 200 nm, and in many cases the beams having wavelengths of 196 nm or less. Hence, the invention may find applications in measuring of deep UV energy beams, including energy which may previously have been thought to be incompatible with position sensing diode structures. Measurements may be obtained of beams having pulse frequencies of up to 50 Hz, the pulses often having a frequency of up to 100 Hz or more, and in many cases having a frequency of up to 1 KHz. Measurement of longer wavelengths of light and/or longer pulse times (or continuous wave beams) may also be effected.

While the present invention may find its most immediate application in measuring and calibrating pulsed laser energy delivery from a refractive surgery system, the invention may also find applications in a wide variety of other industries. Lasers used for semiconductor fabrication, cutting, welding, machining, profilometry, military ranging, and other medical applications such as cosmetic surgery, tissue slicing, cancer treatments, may be measured using the techniques described herein, for example. Hence, the invention may find applications in a number of very different settings.

Figure 1:
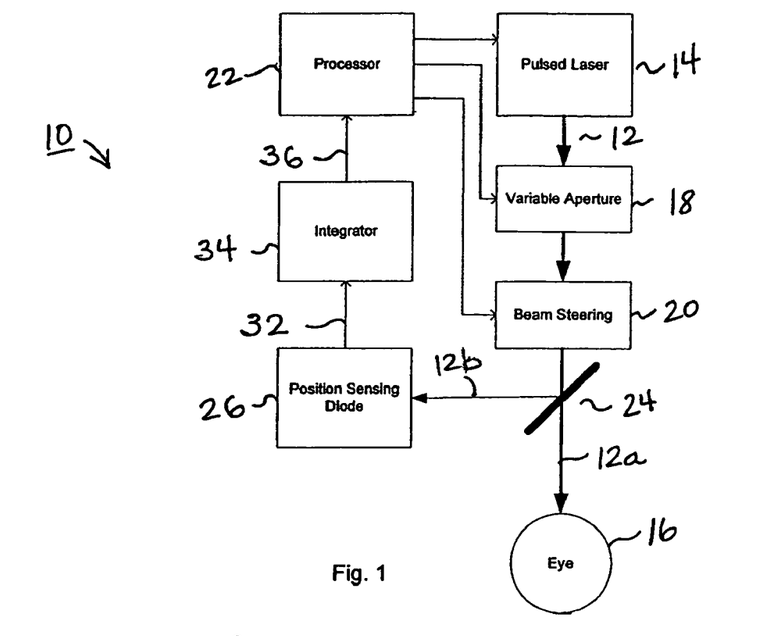
FIG. 1 is a schematic block diagram illustrating an apparatus, system, and method for using a position sensing diode (PSD) to measure a position of a laser in a laser eye surgery system.

Referring now to FIG. 1, a laser eye surgery system 10 generally directs a pulsed laser beam 12 from a laser 14 to an eye 16 so as to alter the refractive properties of the eye. Elements of system 10 may be useful for enhancing the accuracy and efficacy of a variety of laser eye surgical procedures, including photorefractive keratectomy (PRK), laser assisted subepithelial keratomileusis (LASEK), phototherapeutic keratectomy (PTK), laser in situ keratomileusis (LASIK), and the like.

Laser 12 generally comprises an excimer laser, ideally comprising an argon-fluorine laser producing pulses of laser light having a wavelength of approximately 193 nm. Laser 14 will preferably be designed to provide feedback stabilized fluence at the patient's eye of approximately 160 mJoules per $cm^2$, delivered via delivery optics including a variable aperture 18 and a beam steering device 20. The present invention may also be useful with alterative sources of ultraviolet or infrared radiation, particularly those adapted to controllably ablate the corneal tissue without causing significant damage to adjacent and/or underlying tissues of the eye. In alternate embodiments, the laser beam source may employ a solid state laser having a wavelength between 193 and 215 nm, as described in U.S. Pat. Nos. 5,520,697 and 5,144,630 (to Lin) and U.S. Pat. No. 5,742,626 (to Mead). In other embodiments, the laser source may comprise an infrared laser as described in U.S. Pat. Nos. 5,782,822 and 6,090,102 (to Telfair).

Laser 14 and the delivery optics of system 10 will generally direct beam 12 to the eye of a patient under the direction of a processor 22. Processor 22 will often selectively adjust beam 12 to expose portions of the cornea to pulses of laser energy so as to effect a predetermined sculpting of the cornea and alter the refractive characteristics of the eye. Laser 14, variable aperture 18, and beam steering device 20 may be under the control of processor 22 so as to effect the desired laser sculpting process, with the processor effecting (and optionally modifying) a pattern of laser pulses.

Additional components and subsystems may be included with system 10, including spatial and/or temporal integrators, ablation element evacuators/filters, aspirators, eye trackers, and other components of known laser surgery systems. Suitable laser eye surgery systems for use with the beam position sensing components of the invention include those manufactured and/or sold by VISX, Alcon, Bausch & Lomb, Nidek, Wavelight, LaserSight, Schwind, Zeiss-Meditec, and the like. Exemplary laser systems are described in U.S. Pat. Nos. 6,755,818; 6,331,177 and 6,322,216; the full disclosures of which are incorporated herein by reference.

As illustrated in FIG. 1, a beam splitter 24 is disposed along an optical path of beam 12 between laser 14 and eye 16. More specifically, beam splitter 24 is disposed after many of the optical components of the laser delivery system, including variable aperture 18 and beam steering device 20. Beam splitter 24 may comprise, for example, a mirror which transmits a portion of the energy of laser beam 12 along a first optical path 12a while redirecting another potion of the laser energy along a second optical path 12b. Only a small portion of the overall energy may be directed away from eye 16, and the path associated with the eye may be redirected by the mirror so that a slightly transmissive mirror may be used as a beam splitter 24. As the bulk of the energy will be delivered to the eye 16, first path 12a may be described as the "primary" path while second path 12b may be described as the beam monitoring path.

The portion of the laser beam 12 transmitted from beam splitter 24 along monitoring path 12b is directed to a position sensing diode (PSD) 26. More specifically, as can be understood with reference to FIGS. 1 and 2, each pulse of the laser beam 12 results in formation of a laser spot 28 on a sensing surface 30 of PSD 26. As beam splitter 24 is disposed downstream of beam steering device 20, the location of the spot 28 on sensing surface 30 will vary with the position of the beam relative to eye 16. Similarly, as beam splitter 24 is downstream of variable aperture 18, a size and total light quantity of the pulse will vary with the size of the light beam incident on the eye.

As illustrated in FIG. 1, rather than directly determining a position of the beam from a signal produced by the position sensing diode, system 10 transmits an initial signal 32 from the position sensing diode 26 to an integrator 34. Integrator 34 integrates the signal 32 for at least one pulse of the laser beam so as to generate a charge signal 36. It is this charge signal 36 which is used by processor 22 to determine a position of the laser beam. Although sometimes described as an "initial" signal, signal 32 may be subjected to preprocessing prior to integration by integrator 34. Nonetheless, signal 32 remains an "initial signal," in contrast to the integrated or charge signal 36 from integrator 34.

PSD 26 generally comprises a silicon photodiode having a one or two-dimensional sensing surface. Silicon photodiodes may generate an analog output which is directly proportional to a position of a continuous wave of a light spot within a standard wavelength range of the PSD, typically between about 400 and 1100 nm. A light spot within such a spectral range will generate a photo current which flows from the incident point of the light spot through resistive layers separated by a p-n junction. Within this standard wavelength range, the signals output from the PSD may be highly linear, with non-linearity being reported as better than 1%, as defined by the geometric position error divided by the detector length. Unfortunately, for many applications such as laser eye surgery system 10, the wavelength of laser beam 12 may be outside the standard spectral range of PSD 26.

Exemplary PSD structures are commercially available from a number of sources, including ON-TRAK PHOTONICS, INC. of California; SITEK ELECTED OPTICS of Sweden; PACIFICA SILICON SENSOR, INC. of California; and others. Suitable embodiments for monitoring a position of a refractive laser beam in system 10 include model number/name DL-100-7-KER SMD, modified by removing the glass cover and substituting a fused silica cover that is transparent to UV light.

Referring once again to FIG. 2, PSD 26 has first and second X electrodes 40, 42, and first and second Y electrodes 44, 46. Each electrode is coupled to an associated integration circuit 48 of integrator 34. Integrator circuits 48 comprise analog circuits which sum the charge for their associated electrode. It is this summed charge signal which is passed on to processor 22, and more specifically to a position module 50 of the processor. Hence, the initial signal 32 may comprise a plurality of signals from electrodes 40, 42, 44 and 46, or the like. Similarly, integrated signal 36 may comprise a plurality of integrated signals associated with the electrodes.

Figure 2:
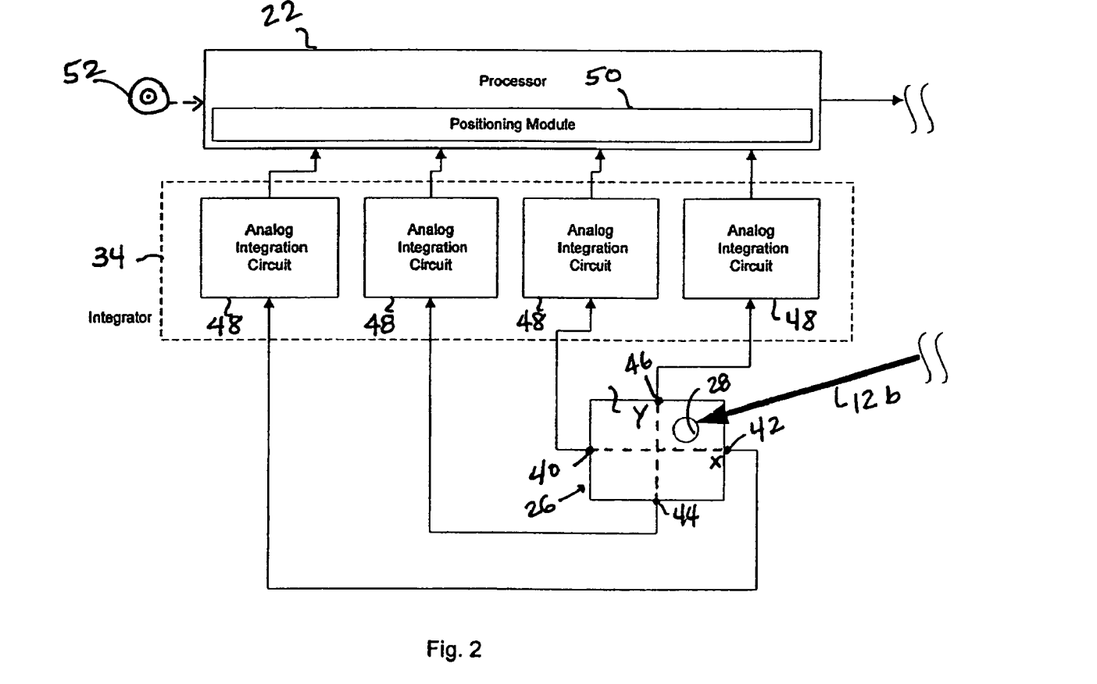
FIG. 2 is a schematic block diagram illustrating a position sensing diode having a plurality of electrodes in which an integrator integrates the signal from each electrode and transmits that signal to a position calculating module of a processor, as may be used in the system of FIG. 1.

Processor 22 typically includes at least one computer processor which may communicate with a number of peripheral devices via a bus system. The peripheral devices may include a storage subsystem, a memory subsystem, a file storage subsystem, a user interface input device, a user interface output device, a network interface subsystem, and the like. Some of these peripheral devices may be used to download a computer executable code from a tangible storage media 52 embodying any of the methods of the present invention. Tangible media 52 may also store data for use in these methods, including correlations between signals transmitted to the processor and beam locations and/or other beam characteristics.

The functionality of processor 22 may be implemented using a series of modules, with each module comprising hardware and/or software. For example, position module 50 may comprise machine readable code including software subroutines for calculating a position of spot 28 on sensor surface 30 of PSD 26 in response to integrated signals from each electrode as provided by integrator 34. Position module 50 may also include hardware components of the processor, such as one or more analog-to-digital converter, one or more integrated circuit processor boards for implementing the position calculation software, and the like. The components of position module 50 and processor 22 in general need not be included within a single housing, but may instead be distributed in a wide variety of data processing architectures. Similarly, the software implementing the method steps described herein may be written as a single continuous code, or as a variety of subroutines. The hardware and software will often be integrated into the hardware and software used for other functions by processor 22. Processor 22 itself can include any of a variety of processor types, including a personal computer, a portable computer, a work station, a computer terminal, a network computer, a control system of a laser surgical system, a main frame, or any other variety of data processing structures Referring once again to FIG. 2, when a pulse of laser energy is incident on sensing surface 30 of PSD 26, the PSD produces a photo charge which varies with the total amount of ultraviolet light in the pulse. Optionally, the photo charge may be proportional to the total amount of light in the pulse. This total charge is distributed to the X and Y electrodes 40, 42; 44, 46 of PSD 26 according to the position of the laser pulse spot 28 on sensor surface 30.

Figure 3:
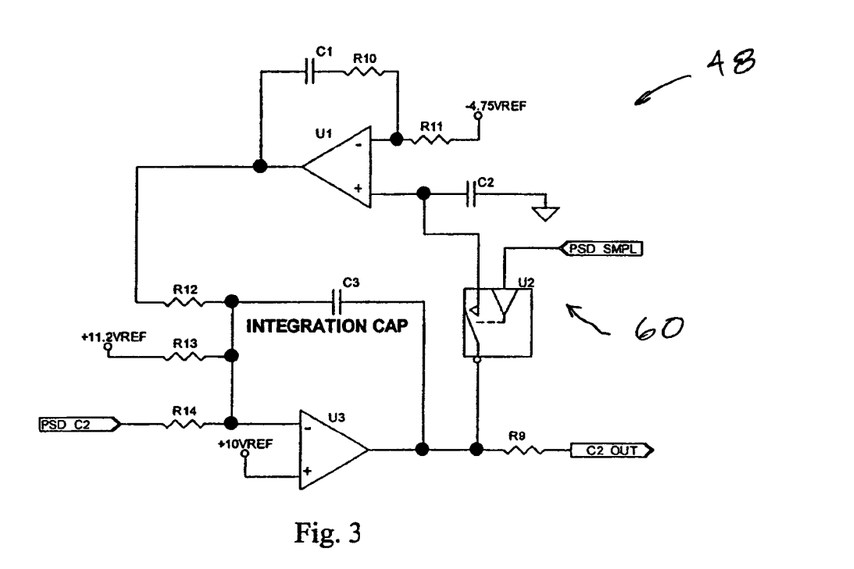
FIG. 3 is a circuit diagram illustrating an exemplary analog integration circuit for use in the integrator of FIG. 2.

Referring now to FIG. 3, an exemplary analog integration circuit 48 converts a portion of the total charge generated by PSD 26 associated with one particular electrode to a voltage at an output C2 OUT. Integrator circuit 48 illustrated in FIG. 3 may be used, for example, as a second channel ("C2" or C2 OUT) or electrode, so that the input from PSD is indicated as PSD C2, and the like. Capacitor C3 generally serves as an integration capacitor, storing the charge delivered by the associated electrode of the PSD. Low leakage of capacitor C3 is beneficial to preserve the charge signal until it is used. The output signal at C2 OUT may be directly proportional to the value capacitance of capacitor C3 for a given charge from the PSD. Operational amplifier U3 buffers capacitor C3 and reverse biases the PSD, which may enhance proper operation.

As capacitor C3 and operational amplifier U3 may hold the charge from the PSD for many pulses, a maximum pulse rate that could be input into integrator circuit 48 could be quite limited. So as to allow the desired laser pulse rates, a reset loop resets the integration circuit between pulses. Analog switch U2, when closed, causes operational amplifier U1 to drive the output of operational amplifier U3 to a reference voltage, here to −4.75 volts. When analog switch U2 is open, operational amplifier U3 and integration capacitor C3 are allowed to integrate the signal transmitted from the PSD electrode. More specifically, capacitor C2 absorbs the charge injection from analog switch U2 and holds the output of operational amplifier U1 steady while the PSD signal is being integrated.

Resistor R10 and capacitor C1 tune the frequency response of operational amplifier U1. Resistor R9 isolates the output from any cable capacitance that might be present. Hence, the output C2 OUT is ready to be digitized by an analog-to-digital converter, and for further processing by processor 22.

Figure 4:
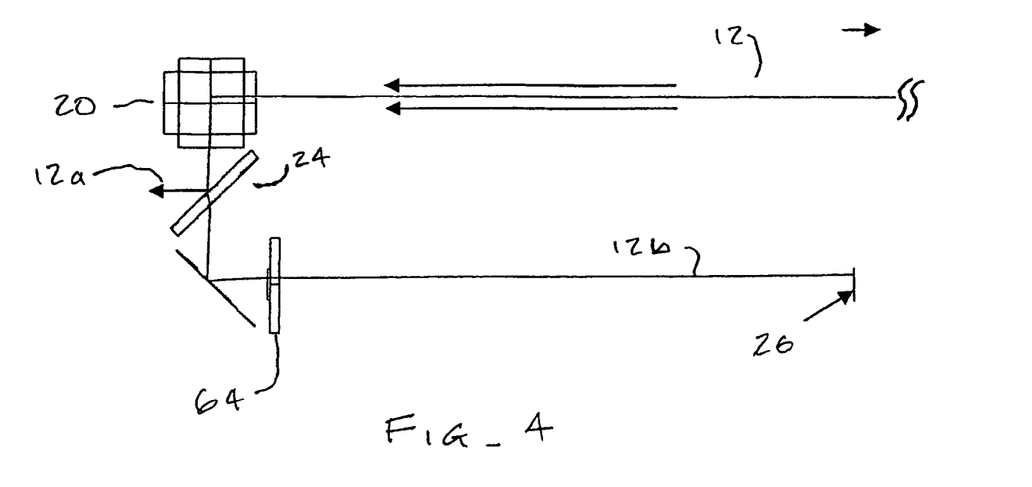
FIG. 4 schematically illustrates a portion of an optical train of a laser eye surgery system which may make use of the system with FIG. 1.

An alternative arrangement for laser eye surgery system having the position sensing diode of the present invention is illustrated in FIG. 4. In this embodiment, the beam steering device 20 may comprise, for example, deflecting mirrors driven by galvanometers or other electromechanical actuators. Once again, other optical elements that position or treat pulses in a laser surgery system upstream of the beam splitter may be monitored.

As the light energy distribution is the same for the primary beam optical path 12a and the monitoring path 12b prior to beam splitter 24, a substantially comprehensive measurement of the energy location delivered in the surgical environment may be obtained, particularly when few or no optical components are disposed along primary optical path 12a downstream of beam splitter 24. Thermal effects and other optical characteristics of the laser delivery system can also be monitored.

In the embodiment of FIG. 4, beam splitter 24 comprises a fixed turning mirror, and may be disposed, relative to the optical components, at or adjacent to a delivery position from the laser system to the eye. Mirror beam splitter 24 transmits a controlled amount of light energy along beam monitoring path 12b, thereby removing this portion of the laser energy from the principal path. The back surface of the turning mirror may allow passage of the transmitted portion of the beam in all beam steering positions, aperture configurations, and the like. Optionally, in extreme offset locations at the treatment plane, some partial clipping of the beam transmitted along monitoring path 12b may occur. So as to avoid a positional error and an uneven energy profile at position sensing diode 26, the position command signal may indicate when such clipping conditions would most likely occur. As not every pulse of the laser system need be individually monitored, such clipped pulses may be disregarded. Alternatively, moving averages or other signal processing methods may be implemented to tighten down on the positional accuracy even when some pulses are not checked.

In light of the size of position sensing diode 26 and space constraints within laser eye surgery systems, the secondary path may not be a complete copy of the primary path. While it is advantageous to have any aperture or the like along the optical path accurately imaged at the sensor surface of position sensing diode 26, a lens 64 may be disposed in monitoring path 12b so as to allow the beam to focus at the desired plane within the space constraints. Employing a shorter focal length lens on the image of the monitoring path 12b may increase spherical aberration (resulting in a less flat intensity profile), decrease the range of motion during scanning and decrease resolution of the sensed position of the beam. Longer focal length lenses will increase the scanning range and improve the resolution of measurement, and may also be utilized. Nonetheless, accurate beam monitoring may be implemented, with scanning range and the like of the monitor beam typically being correlated to the desired laser delivery pulse pattern by the processor 22.

Position sensing diode 26 may optionally comprise a one-dimensional position sensing diode but will typically comprise a two-dimensional position sensing diode. Optionally, the ultraviolet radiation of beam 12 may directly strike the sensor surface of the PSD, inducing a signal directly from the chip. Alternatively, a protective cover may extend over the position sensing diode. In some embodiments, the protective cover may luminesce in response to UV excitation, with the luminescence passing from the cover to the sensor surface. This may reduce or eliminate UV radiation striking the sensor surface. In this configuration, the UV radiation induces light from the cover, with this induced cover light providing the light detected by the chip, the induced light typically being within the standard wavelength range of the PSD while the UV laser energy is not. In still further alternative embodiments, a protective cover may pass a portion of the UV radiation of the monitoring beam without exciting a significant luminescence, the UV radiation inducing a signal directly from the chip with the cover providing an enhanced life for the position sensing diode or the like.

Position sensing diode 26 may optionally produce two pairs of signals, one pair (of signals) for the X position and one pair for the Y position. Each signal is integrated by the integrators 48. The energy of a laser pulse may be obtained by combining the components of either pair of integrated signals; either the two X position integrated signals or the two Y position integrated signals. To detect position, the same pair of integrated signals can be combined in a different way; the two X positions integrated signals can provide the X position of the incident laser pulse and the two Y position integrated signals can provide the Y position of the incident laser pulse The systems and methods described above are particularly useful for monitoring and verifying beam steering effected by one or more mirrors driven using galvanometers. Galvanometers may have good stability within a temperature range, but the temperature range and temperature variation may differ for different individual beam steering units. While temperatures of the galvanometers may be monitored using thermocouples, thermistors, or other temperature sensors, the structures and methods described above can be used to provide direct feedback on actual beam steering to the processor directing the pattern of laser energy intended to produce a refractive correction.

The beam position monitoring devices and methods described above may be used during alignment of and adjustment to the optical components of the laser delivery system, as well as during treatment. For example, center drift of an iris during opening and closing may be determined, beam uniformity during temporal integration, and any oscillation of the beam induced by rotation of the delivery optics about the beam axis may be measured and corrected before and/or between treatments.

While use of the initial signal taken directly from a position sensing diode (as generated from light within the standard operating range of the PSD) may be both linear (continuous signal output relative to beam position) and unaffected by different spot sizes, the integrated signal techniques described herein may benefit from correlations which vary with differing spot sizes, and will often comprise correlations which are non-linear (having a non-fixed slope). Hence, the correlation may comprise, for example, a series of different curves correlating integrated signals to beam locations at different spot sizes. These correlations may be readily generated by empirical testing of the devices described above.

The quantity of charge produced in the PSD increases with increasing incident laser pulse energy. The proportion of this charge that flows through an edge (electrode) of the PSD is related to the proximity of the pulse to the edge. For a one-dimensional PSD there are two opposed edges, each of which provides a pulse of current to its integrator. The current is integrated by the integrator to provide a signal that is proportional to the charge that has flowed through that edge. The signals can be referred to as $S_l$ (left signal) and $S_r$ (right signal). The laser pulse energy is thus related to $$(S_l + S_r). \qquad \text{Formula 1}$$

The relationship is likely to be non-linear due to charge recombination and saturation within the PSD and other phenomena.

The distance of the center of the laser pulse from the left edge of the PSD is given by $$S_r \times D/(S_l + S_r) \qquad \text{Formula 2}$$

where D is the total length of the PSD. For a two dimensional PSD, the same formulation can be applied and the signals from the X and Y pairs of integrators can be considered to be independent. For instance for top and bottom electrodes, the distance of the laser spot from the top electrode would be given by $$S_b \times D/(S_t + S_b) \quad \text{Formula 3}$$

where $S_b$ is bottom signal, $S_t$ is top signal, and D is total length of the PSD.

Figure 5:
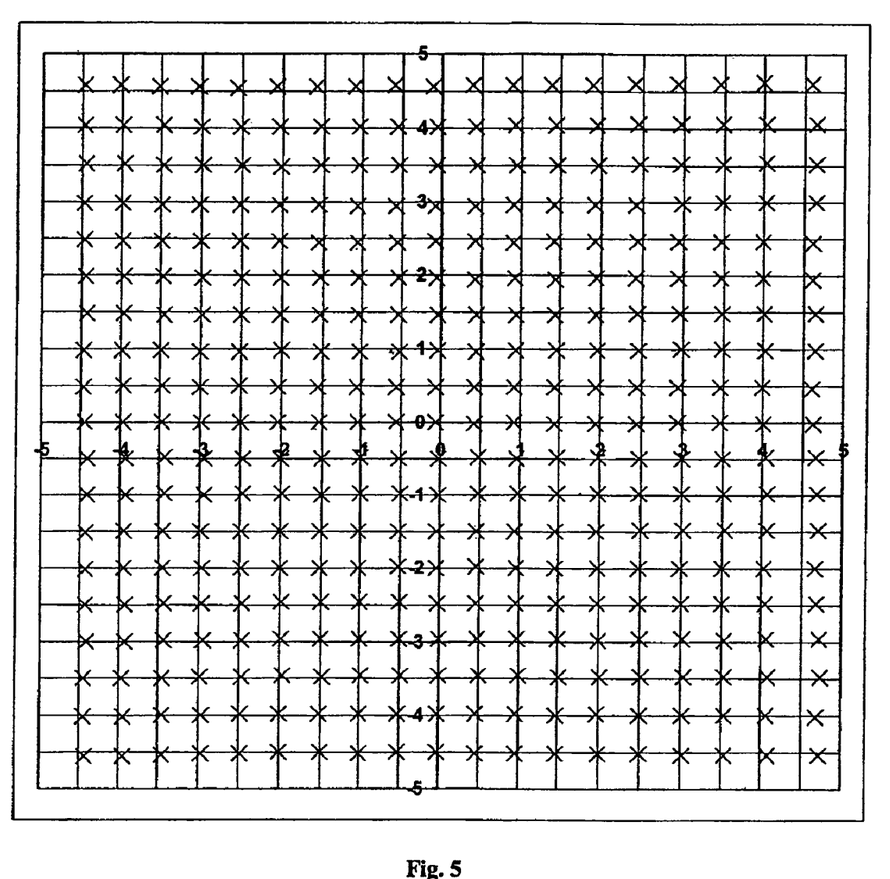
FIG. 5 graphically illustrates a grid of pulses corresponding to a laser pulse fired at 0.5 mm steps in both X and Y directions.

As shown in FIG. 5, a single 5 mm diameter laser pulse of 193 nm wavelength of with an energy density of approximately 160 mJ/cm$^2$ was fired at 0.5 mm steps from −4.5 mm to +4.5 mm (in the treatment plane) in both X and Y directions. In this illustration, the energy density of the laser pulse as it lands on the PSD is 2% of the approximately 160 mJ/cm$^2$. This grid of pulses covers the entire range of possible extents of pulses that could be fired during a treatment. Positions were calculated using the Formulae 1, 2 and 3 but adjusted to give a best fit to the actual firing positions by using a linear scaling factor and an offset value in both dimensions. These two pairs of fitting parameters can be used for subsequent sequences of pulses as calibration constants. The root mean square error of the entire sequence of pulses shown in FIG. 5 is 66 microns. This value can be reduced by removing pulses at the edges of the PSD that are either very close to the edge or clipped by the edge of the PSD. As shown in the top right portion of FIG. 5, pulses are slightly clipped by components of the optical train which also results in a small amount of distortion. Using this calibration method, the RMS error for a subsequent series of 5 mm pulses fired during an actual treatment is expected to be less than 50 microns. It may be desirable to individually calibrate each laser pulse diameter using this simple linear calibration method due to the non-linearity of the PSD's response to pulse energy. More complex calibration methods that use non-linear terms or that calibrate the individual integrated signals directly may also be employed.

While exemplary embodiments have been described in some detail for clarity of understanding, a variety of modifications, changes, and adaptations will be obvious to those of skill in the art. Hence, the scope of the present invention is limited solely by the appended claims.

What is claimed is:

1. An apparatus comprising:
  a light source for directing a pulsed light beam along an optical path, wherein a wavelength of the pulsed beam is less than 200 nm;
  an analog position sensing diode disposed in the optical path so as to generate an analog signal in response to a pulse of the beam;
  an integrator coupled to the position sensing diode so as to integrate the signal for the pulse to generate a charge signal; and
  a position module coupled to the integrator, the position module configured to determine a position of the pulse on the position sensing diode in response to the charge signal.

2. The apparatus of claim 1, wherein the light source comprises an excimer laser and the pulsed laser beam has a wavelength in a range from about 190 nm to about 196 nm.

3. The apparatus of claim 1, further comprising a beam deflector disposed along the optical path from the light source and a beam splitter disposed along the optical path from the beam deflector, the beam splitter separating the beam and directing a first portion of the beam along the optical path toward the position sensing diode and a second portion of the beam along another optical path, wherein the beam deflector variably redirects the beam so that the position module indicates a position of the second portion of the beam.

4. The apparatus of claim 1, wherein the position sensing diode has a sensing surface and a plurality of electrodes, wherein the integrator is coupled to at least two of the electrodes, and wherein the signal has a total charge associated with the pulse, wherein the integrator generates the charge signal by summing at least two portions of the total charge directed to an associated at least two electrodes, and wherein the pulse position is determined using the at least two charge portions.

5. The apparatus of claim 4, wherein the integrator sums a plurality of charge portions at an associated plurality of electrodes, wherein the position module is configured to determine a total charge at the plurality of electrodes, the total charge correlating to an amount of light at the sensing surface of the position sensing diode, and wherein the position module is configured to apply a correlation between the pulse position and a distribution of the charge portions between the plurality of electrodes.

6. The apparatus of claim 5, wherein the position module is configured to determine a position of the pulse along an X axis of the sensing surface from a distribution of the total charge between a first X electrode and a second X electrode.

7. The apparatus of claim 6, wherein the sensing surface comprises an X-Y sensing surface, and wherein the position module is configured to determine a position of the pulse along a Y axis of the sensing surface from a distribution of the total charge between a first Y electrode and a second Y electrode.

8. The apparatus of claim 1, wherein the position sensing diode comprises a silicon photodiode having a plurality of electrodes, and wherein the integrator comprises a plurality of analog integrator circuits, each integrator circuit coupled to an associated electrode.

9. The apparatus of claim 1, wherein the positioning module is configured to determine a plurality of positions of a plurality of pulses of the beam, the integrator being reset between at least some of the pulses.

10. An apparatus for altering a refraction of an eye, the apparatus comprising:
  a laser for directing a pulsed laser beam along an optical path, the laser beam having a wavelength of less than about 220 nm;
  a beam deflector disposed along the optical path from the laser, the beam deflector variably redirecting the beam;
  a beam splitter disposed along the optical path from the beam deflector, the beam splitter separating the laser beam and directing a first portion of the laser beam along the optical path and a second portion of the laser beam along another optical path toward the eye;
  a position sensing diode disposed in the optical path so as to generate a signal in response to a pulse of the laser beam;
  an integrator coupled to the position sensing diode so as to integrate the signal for the pulse to generate a charge signal; and
  a position module coupled to the integrator, the position module configured to indicate a position of the beam on the eye in response to the charge signal.

11. The apparatus of claim 10, further comprising a variable aperture for varying a size of a laser spot and the eye during a refractive treatment, wherein the position module determines the position in response to the laser sport size.

12. A method for determining a position of a pulsed beam, the pulsed beam suitable for ablation of corneal tissue, the method comprising:
  positioning a position sensing diode in a path of the beam;

generating, with the position sensing diode, an initial signal in response to a pulse of the beam;

integrating the initial signal for the pulse to generate an integrated charge signal; and determining a position of the pulse on the position sensing diode in response to the integrated signal. beam having a wavelength of less than 220 nm.

13. The method of claim 12, wherein the pulsed laser beam has a wavelength in a range from about 190 nm to about 196 nm.

14. The method of claim 1, wherein the pulsed beam is capable of photoablating corneal tissue.

15. The method of claim 14, further comprising separating the beam and directing a first portion of the beam along the optical path toward the position sensing diode and a second portion of the beam along another optical path toward an eye of a patient so that the beam changes a refraction of the eye while a position of the beam on the eye is determined using the position sensing diode.

16. The method of claim 12, wherein the pulsed beam is generated using an excimer laser.

17. The method of claim 12, wherein the position sensing diode has a sensing surface and a plurality of electrodes, wherein the initial signal has a total charge associated with the pulse, wherein the integration sums at least two portions of the total charge directed to an associated at least two electrodes, and wherein the pulse position is determined using the at least two charge portions.

18. The method of claim 17, wherein the integration of the initial signal comprises summing a plurality of charge portions at the plurality of electrodes, wherein the pulse position is determined using a distribution of the charge portions between the plurality of electrodes.

19. The method of claim 18, further comprising determining a total amount of light at the sensing surface of the position sensing diode from the charge portions at the plurality of electrodes.

20. The method of claim 19, wherein a position of the pulse along an X axis of the sensing surface is determined using a correlation between the X position and a distribution of the total charge between a first X electrode and a second X electrode.

21. The method of claim 20, wherein the correlation is non-linear.

22. The method of claim 20, wherein the sensing surface comprises an X-Y sensing surface, and wherein a position of the pulse along a Y axis of the sensing surface is determined using a correlation between the Y position and a distribution of the total charge between a first Y electrode and a second Y electrode.

23. The method of claim 22, wherein the correlation is non-linear.

24. The method of claim 12, wherein the position sensing diode comprises a silicon photodiode having a plurality of electrodes, and wherein the initial signal is integrated using a plurality of analog integrator circuits, each integrator circuit coupled to an associated electrode.

25. The method of claim 12, wherein the integration is performed by an integrator, and further comprising: determining a plurality of positions of a plurality of pulses of the beam; and resetting the integrator between at least some of the pulses.

26. The method of claim 25, wherein the pulsed beam has a frequency of up to 1 KHz.

27. The method of claim 12, wherein the initial signal is integrated by at least one analog integrator circuit.

* * * * *